(12) United States Patent
Della Valle et al.

(10) Patent No.: US 8,546,352 B2
(45) Date of Patent: Oct. 1, 2013

(54) PHARMACOLOGICAL PREPARATION FOR TOPICAL USE CONTAINING N-PALMITOYL-VANILLAMIDE

(75) Inventors: Francesco Della Valle, Padua (IT);
Luciano De Petrocellis, Napoli (IT);
Sabatino Maione, Napoli (IT);
Vincenzo Di Marzo, Napoli (IT); Maria Federica Della Valle, Padua (IT)

(73) Assignee: Epitech Group S.r.l., Milan (IT)

( * ) Notice: Subject to any disclaimer, the term of this patent is extended or adjusted under 35 U.S.C. 154(b) by 8 days.

(21) Appl. No.: 13/291,294

(22) Filed: Nov. 8, 2011

(65) Prior Publication Data
US 2012/0115808 A1 May 10, 2012

(30) Foreign Application Priority Data
Nov. 8, 2010 (EP) .................................... 10190375

(51) Int. Cl.
*A61K 31/165* (2006.01)
(52) U.S. Cl.
USPC ......................................................... 514/54
(58) Field of Classification Search
USPC .......................................................... 514/54
See application file for complete search history.

(56) References Cited

U.S. PATENT DOCUMENTS
7,645,767 B2 * 1/2010 Singh et al. .................... 514/282

OTHER PUBLICATIONS
De Filippis et al. Adelmidrol, a palmitoylethanolamide analogue, reduces chronic inflammation in a carrageenin-granuloma model in rats. J Cell Mol Med 13:1086-1095, 2009.*

* cited by examiner

*Primary Examiner* — Wu-Cheng Winston Shen
*Assistant Examiner* — Yih-Horng Shiao
(74) *Attorney, Agent, or Firm* — Pearl Cohen Zedek Latzer, LLP

(57) ABSTRACT

The present invention relates to topical preparations containing N-palmitoyl-vanillamide having hyperalgesic activity. In particular, the invention relates to N-palmitoyl-vanillamide for use in the treatment of pathologies selected from: post-herpetic neuralgia, neuralgia of trigeminus, occipital neuralgia, dental neuralgia, glottopharyngeal neuralgia, uremic neuralgia, diabetic neuralgia, headache of different origin, neuropathic itch, neurogenic itch, uremic itch, vulvodinia, vulvar vestibulitis, ano-rectal pain and itch, balano-preputial pain and itch, painful urogenital disorders of dogs and cats, psoriasis-associated pruritus and pain, itching skin diseases (e.g. atopic dermatitis) in the human and veterinary field, muscular pain, pain of the tendon, osteoarthritis associated pain in humans, dogs and cats; painful eye diseases in the human and veterinary field, inflammatory pathologies of the oral cavity in the human and veterinary field.

9 Claims, 5 Drawing Sheets

US 8,546,352 B2

PHARMACOLOGICAL PREPARATION FOR TOPICAL USE CONTAINING N-PALMITOYL-VANILLAMIDE

PRIOR APPLICATION DATA

This application claims priority to and benefit of European Patent Application 10190375.5, filed on Nov. 8, 2010, incorporated by reference herein in its entirety.

FIELD OF THE INVENTION

The present invention relates to a topical preparation containing N-palmitoyl-vanillamide with anti-hyperalgesic activity.

BACKGROUND

The transient receptor potential of vanilloid type-1 (TRPV1) channel is a non-specific cation channel and plays a major role in nociceptive heat thermosensation and inflammatory hyperalgesia. It is abundantly expressed in unmyelinated sensory fibers of the Aδ- and C-type as well as in the spinal cord, and its activation in the peripheral afferents of dorsal root ganglia causes entry of calcium, depolarization and local release of algogenic peptides, such as calcitonin gene-related peptide and substance P, as well as activation of ascending pathways of pain transmission. The TRPV1 channel was discovered thanks to studies on the mechanism of action of the pro-nociceptive and thermal pain-mimicking actions of capsaicin, the pungent principle of *Capsicum annum*. Apart from being up-regulated during chronic pain conditions, TRPV1 exists in several phosphorylated/active and dephosphorylated/inactive forms, only the former of which are capable of mediating the gating of extracellular calcium into neurons through channel pores and subsequent depolarization. TRPV1 phosphorylation can be triggered by several algogenic mediators through the intermediacy mostly of protein kinases C and A, and, together with release of the channel from the tonic inhibitory action of phosphatidyl-inositol-bis phosphate, obtained through PI3 kinase or phospholipase C activation, it is the major molecular mechanism for its sensitization to the action of temperature, low pH (protons), endogenous agonists (endovanilloids) and toxins like capsaicin. Calcium entry also causes the desensitization of the channel, through the action of $Ca^{2+}$-sensitive protein phosphatases such as calcineurin. Therefore, TRPV1 is made refractory by its agonists to further stimulation by noxious heat or endogenous algogenic mediators, thus leading to paradoxical anti-hyperalgesic actions, which are at the basis of the use of capsaicin-based creams against chronic pain.

SUMMARY

It has now been discovered that N-palmitoyl-vanillamide, known by the name of Palvanil, which is an highly stable synthetic TRPV1 agonist, is capable of desensitizing TRPV1 from activation operated by exogenous and endogenous pro-nociceptive and pro-inflammatory stimuli, without displaying pungent effects, and showing anti-nociceptive activity in vivo tests of nociception.

It has been observed that, as compared to capsaicin, Palvanil exhibits a slower kinetics of TRPV1 activation, as assessed by monitoring TRPV1-mediated elevation of intracellular calcium in HEK293-TRPV1 cells and is significantly more potent at desensitizing capsaicin- and anandamide/pH-induced activation of TRPV1 in HEK293-TRPV1 cells, its maximal desensitizing effects being observed with more rapid onset. A strong desensitizing effect by Palvanil on anandamide 0.25 microM plus pH 6.5, which somehow mimics conditions that might occur in the "inflammatory pathway", in which TRPV1 is up-regulated, anandamide is overproduced and pH is lowered, was observed at concentrations of Palvanil as low as 0.5 nM, as compared to capsaicin, which exerted a half-maximal inhibition at concentrations 18-fold higher; 3) unlike capsaicin, Palvanil is absolutely not pungent in the eye wiping assay; and 4) although non-pungent per se, Palvanil inhibits in a long-lasting and dose-dependent way the capsaicin-induced response in this assay, in a way antagonized by a TRPV1-antagonist. These are very relevant and innovative results because they indicate that it is possible, with Palvanil, to obtain anti-hyperalgesic pharmaceutical preparations, superior to capsaicin both in efficacy and safety, in diseases characterized by neuropathic inflammation and chronic inflammatory or neuropathic pain, in human and in veterinary field.

DETAILED DESCRIPTION

Figure 1A:
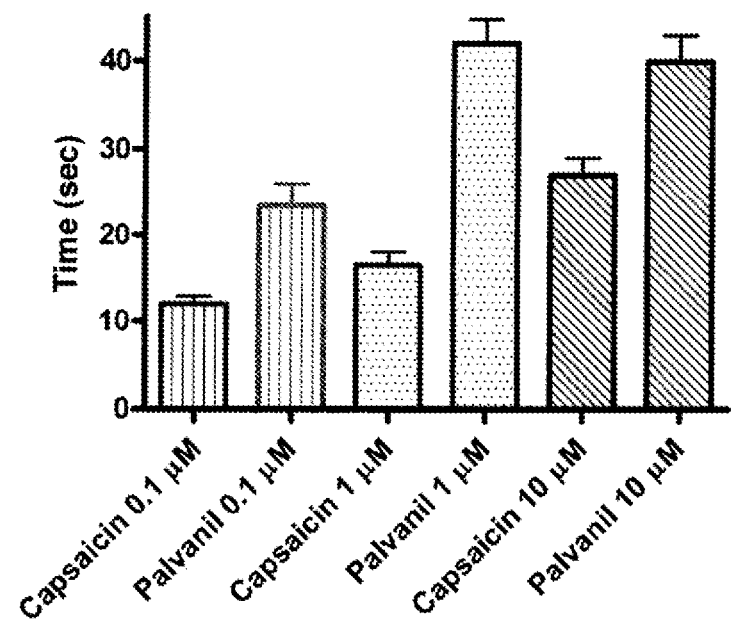
FIGS. 1A and 1B. Kinetics of TRPV1-mediated elevation of intracellular $[Ca^{2+}]$ by capsaicin and Palvanil. (A) Time necessary to produce a maximal elevation of intracellular calcium in HEK-293-TRPV1 cells with different concentrations of Palvanil and capsaicin; (B) kinetics of intracellular calcium elevation by 1 μM capsaicin (continuous line) and Palvanil (dotted line). Arrows denote time of administration of the compounds to cells. In (A) data are means±SEM of n=4 different determinations. The values for Palvanil were always significantly different from those of capsaicin as assessed by ANOVA followed by the Bonferroni's test (P<0.05)
Figure 1B:
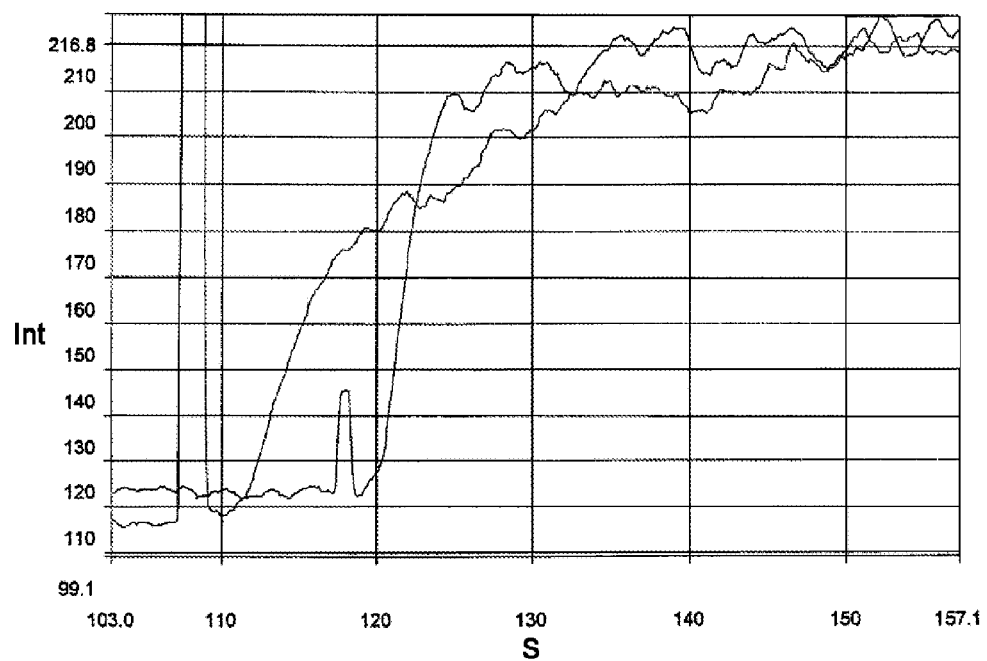

An object of the present invention is N-palmitoyl-vanillamide for use in the treatment of inflammatory and neuropathic hyperalgesia in mammals.

A further object of the invention is N-palmitoyl-vanillamide for use in the treatment of a pathology selected from: post-herpetic neuralgia, neuralgia of trigeminus, occipital neuralgia, dental neuralgia, glossopharyngeal neuralgia, uremic neuralgia, diabetic neuralgia, headache of different origin, neuropathic itch, neurogenic itch, uremic itch, vulvodynia, vulvar vestibulitis, ano-rectal pain and itch, balano-preputial pain and itch, painful urogenital disorders of dogs and cats, psoriasis-associated pruritus and pain, itching skin diseases (e.g. atopic dermatitis) in the human and veterinary field, muscular pain, pain of the tendon, osteoarthritis associated pain in humans, dogs and cats; painful eye diseases in the human and veterinary field, inflammatory pathologies of the oral cavity in the human and veterinary field.

According to an embodiment, the said inflammatory pathologies of the oral cavity in the human are gingivitis, parodontitis, stomatitis, post implantation pain, burning mouth syndrome.

According to an embodiment, the said inflammatory pathologies of the oral cavity in the veterinary field are canine and feline gingivitis, parodontitis, gingivostomatitis, and feline resorptive lesions (FORL).

Another object of the invention is a topical formulation containing N-palmitoyl-vanillamide for use in the treatment of inflammatory and neuropathic hyperalgesia in mammals.

N-palmitoyl-vanillamide is a known drug and can be prepared according to conventional methods, such as the one disclosed in the experimental section of the present description.

The topical composition according to the invention can be in the form of a cream, gel, lotion, drops for otological application, patch, eyewash, mouthwash, suppository or any other suitable pharmaceutical form and may contain conventional excipients. The preparation of the topical composition of the invention can be performed according to well known technologies, such as the ones described in Remington's Pharmaceutical Sciences Handbook, Mack Pub. Co., N.Y., USA, 17th edition, 1985.

The composition may contain additional active principles, such as adelmidrol, trans-traumatic acid, menthol, hyaluronic acid or its salts or vitamin A.

Palvanil can be administered to a subject of about 70 kg of body weight in a dosage between 0.1 mg and 1 g and preferably between 1 mg and 100 mg per dosage unit. The dosage unit may be administered for example from 1 to 4 times a day. The dosage can be adjusted according to the pathology to be treated and the conditions of the patient.

The composition of the invention may contain from 0.05% to 5% w/w of N-palmitoyl-vanillamide.

EXPERIMENTAL PART

Example 1

Preparation of N-palmitoyl-vanillamide (Palvanil)

4.475 g of 4-hydroxy-3-methoxybenzylamine hydrochloride and 0.556 g of 4-methylmorpholine are dissolved in 10 ml of dimethylformamide at 0° C. A solution of 0.605 g of palmitoyl chloride in 5 ml of chloroform is added dropwise slowly over 30 min with continuous stirring.

The resulting mixture is stirred overnight at 0° C. and 25 ml of water are then added and this mixture is extracted 3 times with 10 ml of ethyl acetate.

The organic phases are washed twice with 5 ml of 1N hydrochloric acid and twice with 4 ml of water; the organic phases are then combined, decolorized with animal charcoal, dried over anhydrous sodium sulfate and evaporated under vacuum.

The residue is crystallized from 7 ml of tert-butyl methyl ether; the product, separated out by filtration, is washed twice with 3 ml of cold tert-butyl methyl ether and is finally dried under high vacuum.

The reaction yield is about 91%.

The physicochemical properties of the product N-(4-hydroxy-3-methoxybenzyl)palmitoylamide are as follows:
Physical state: white crystalline powder
Empirical formula: C24H41NO3
Molecular weight: 391.60
Elemental analysis: C=73.61%; H=10.55%; N=3.58%; O=12.26%
Solubility in organic solvents: >10 mg/ml in DMSO; >10 mg/ml in ethanol
Solubility in water: sparingly soluble
TLC: 65/30/5 toluene/ethanol/acetic acid eluent; Rf=0.65.

Assays of TRPV1-Mediated Elevation of Intracellular [Ca2+]

HEK-293 cells stably over-expressing recombinant human TRPV1 were selected by G-418 (Geneticin; 600 µg/ml), grown on 100-mm diameter Petri dishes as monolayers in minimum essential medium supplemented with non-essential amino acids, 10% fetal bovine serum, and 2 mM glutamine, and maintained under 5% CO2 at 37° C. On the day of the experiment, the cells were loaded for 1 h at 25° C. with the cytoplasmic calcium indicator Fluo-4AM (Invitrogen) 4 µM in dimethyl sulfoxide containing 0.02% Pluronic F-127 (Invitrogen). After loading, cells were washed twice in Tyrode's buffer (145 mM NaCl, 2.5 mM KCl, 1.5 mM CaCl$_2$, 1.2 mM MgCl$_2$, 10 mM D-glucose, and 10 mM HEPES, pH 7.4), resuspended in the same buffer, and transferred to a quartz cuvette of the spectrofluorimeter (excitation λ=488 nm; emission λ=516 nm) (Perkin-Elmer LS50B) under continuous stirring. Experiments were carried by measuring cell fluorescence before and after the addition of various concentrations of the compounds. The potency of test compounds (EC50 values) were determined as the concentration of test substances required to produce half-maximal increases in [Ca$^{2+}$]i. The efficacy of the agonists was determined by comparing their effect with the analogous effect observed with 4 µM ionomycin. Antagonist behaviour was evaluated against capsaicin (10 nM) or anandamide 0.5 and 0.25 µM at different pH values by adding the compounds in the quartz cuvette 5 min before the agonist (capsaicin or anandamide). Data were expressed as the concentration exerting a half-maximal inhibition of agonist effect (IC50). The effect on [Ca$^{2-}$]i exerted by the agonist alone was taken as 100%. All determinations were at least performed in triplicate. Dose response curves were fitted by a sigmoidal regression with variable slope. Curve fitting and parameter estimation were performed with GraphPad Prism (GraphPad Software Inc., San Diego, Calif.).

Eye-Wiping Assays in Mice

The pain-inducing potency of Palvanil was determined by the eye-wiping assay in mice, using a protocol similar to that previously described in rats (Szallasi A, Blumberg P M. Neuroscience, 1989; 30: 515-520), and its effect on capsaicin-induced wiping was also evaluated. Male CD1 mice (weight 25 g) were maintained in a controlled lighting environment and groups of 6 animals were used for each treatment. The animals received drugs instillations (10 µl) in the left eye and were used for one treatment only. The number of the eye-wiping movements following drugs instillation into the eye was considered as index of pungency. Moreover, the eye-wiping reflexes in response to capsaicin (10 μg/ml), alone or after Palvanil or the TRPV1 antagonist 5'-iodo-resiniferatoxin (I-RTX), dropped in solution into the eye, was determined during 30 sec after the instillation. The animals were treated as follows:

capsaicin (10 μg/ml)
capsaicin (10 μg/ml)+Palvanil (10 and 30 μg/ml)
I-RTX (1 μg/ml)+Palvanil (10 and 30 μg/ml)+capsaicin (10 μg/ml)
I-RTX (1 μg/ml)

The dose of I-RTX was chosen based on pilot experiments and was the highest dose of the antagonist that did not antagonize the effect of 10 μg/ml capsaicin per se.

Results

Kinetics of TRPV1-Mediated Elevation of Intracellular [$Ca^{2+}$] by Capsaicin and Palvanil Capsaicin and Palvanil were added at different concentrations and produced a dose-dependent increase in intracellular calcium with a EC50=3.9±0.4 nM and 0.65±0.04 nM respectively. When we analyzed the time required for the agonists to achieve 90% of total TRPV1 mediated calcium influx at different concentrations we noted that the activation of TRPV1 by capsaicin was always significantly faster than that obtained by Palvanil, with the greatest difference at 1 μM (FIG. 1A e 1B).

Effect of Palvanil and Capsaicin on Capsaicin-Induced TRPV1-Mediated Elevation of Intracellular [$Ca^{2+}$]

Figure 2:
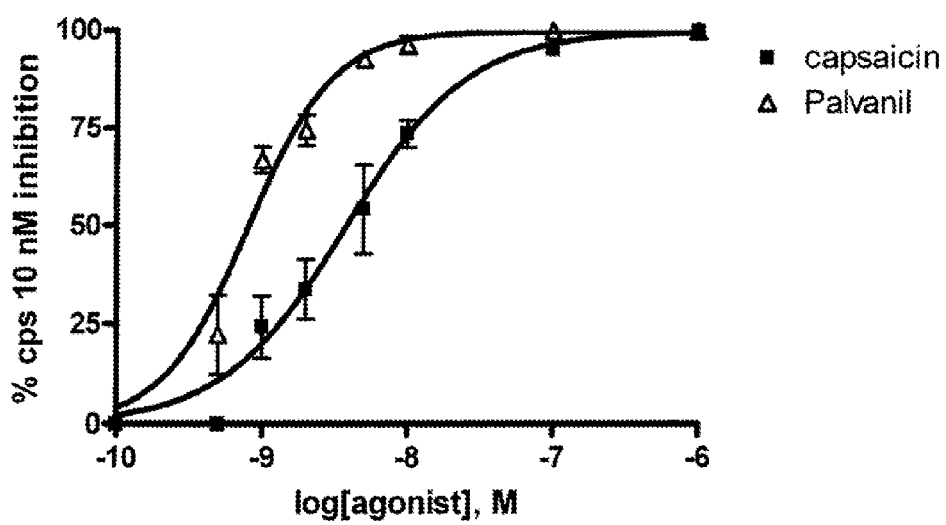
FIG. 2. Dose response curves for the desensitization of capsicin (10 nM) effect on intracellular calcium in HEK-293-TRPV1 cells by capsaicin and Palvanil. Data are means±SEM of n=4 different determinations. The values for Palvanil were significantly different from those of capsaicin in the range of log] [agonist] from −9 to −8, as assessed by ANOVA followed by the Bonferroni's test (P<0.05)

We evaluated the desensitizing effect of Palvanil and capsaicin on TRPV1 mediated intracellular $Ca^{2+}$ elevation induced by 10 nM capsaicin, the two compounds being administered to cells 5 min before exposure to capsaicin. Palvanil desensitized TRPV1 to the effect of capsaicin significantly more potently than capsaicin (IC50 0.81±0.07 and 3.8±0.5 nM, respectively, P<0.01) (FIG. 2).

Figure 3:
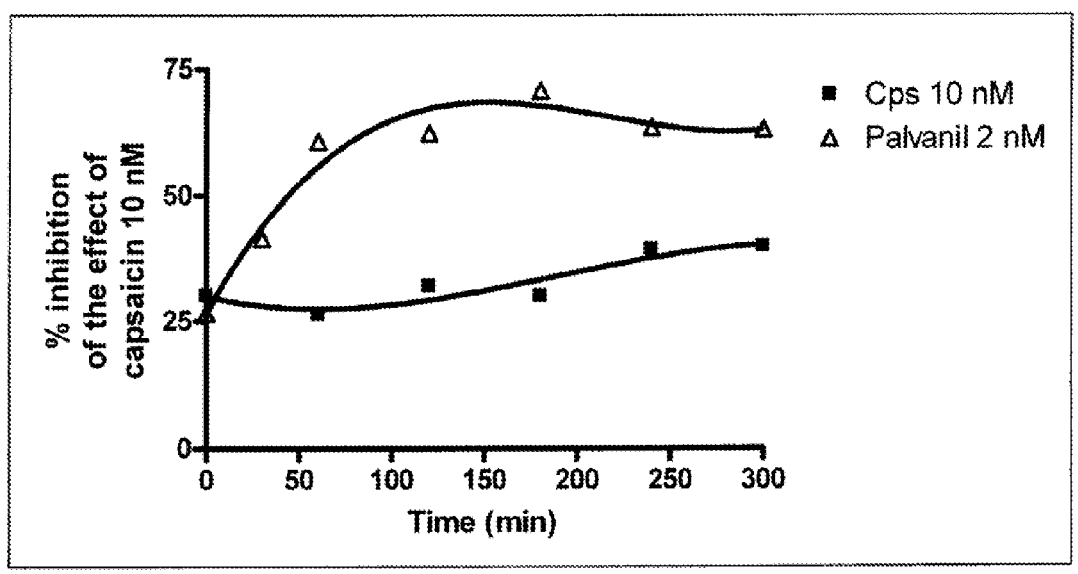
FIG. 3. Extent of the desensitization of capsicin (10 nM) effect on intracellular calcium in HEK-293-TRPV1 cells by capsaicin and Palvanil as measured after different pre-incubation times of cells with either compound. Data are means of n=4 different determinations. SEM bars are not shown and were always <5% of the means. The values for Palvanil were significantly different from those of capsaicin at all times, as assessed by ANOVA followed by the Bonferroni's test (P<0.05)

We next evaluated the influence of the pre-incubation time on the desensitizing effect of the two TRPV1 agonists on 10 nM capsaicin stimulation of TRPV1-mediated elevation of intracellular calcium. The effects of 2 nM Palvanil and 10 nM capsaicin (concentrations which per se produce a similar elevation of intracellular calcium) were compared. Whilst the desensitizing effect of Palvanil reached a maximum about with 50 min pre-incubation, capsaicin produced a significantly less pronounced desensitizing effect, which tended to increase only with 5 hour incubation (FIG. 3). Therefore, Palvanil and capsaicin show different time-dependent desensitizing abilities.

Effect of Palvanil and Capsaicin on Anandamide/Low pH-Induced TRPV1-Mediated Elevation of Intracellular [$Ca^{2+}$]

Figure 4A:
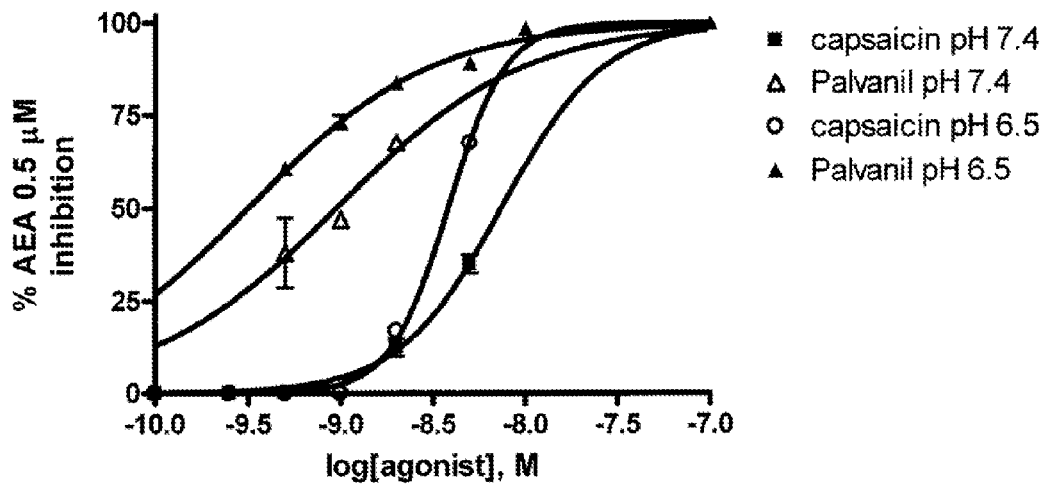
FIGS. 4A and 4B. Dose-dependent effects of Palvanil or capsaicin on the effect on intracellular calcium in HEK-293-TRPV1 cells by anandamide 0.5 μM (A) or 0.25 μM (B) at pH 7.4 and 6.5. Data are means of n=4 different determinations. SEM bars are not shown and were always <5% of the means.
Figure 4B:
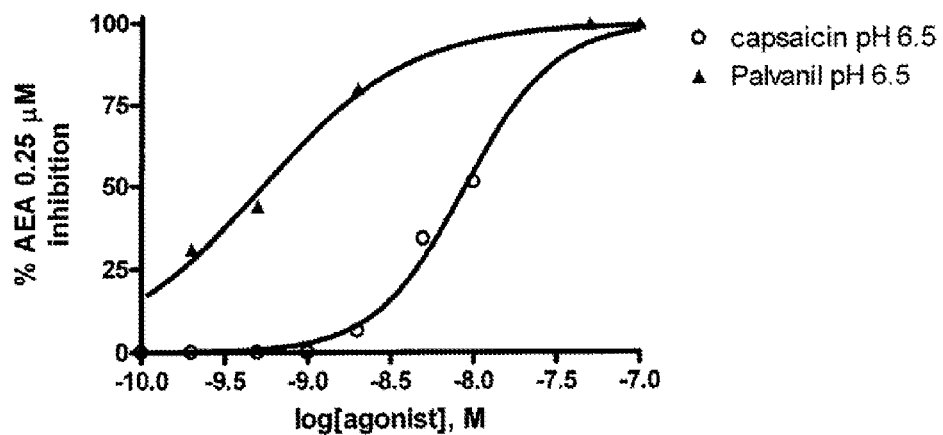

The effects of Palvanil and capsaicin were evaluated on the TRPV1-mediated elevation of intracellular $Ca^{2+}$] induced by the endogenous agonist anandamide at physiological pH (7.4) and at acid pH (6.5). Dose-response curves show that preincubation of both Palvanil and capsaicin have strong desensitizing effects on the activity of 0.5 μM AEA. This effect is more pronounced with Palvanil as compared to capsaicin at both physiological (IC50 0.9±0.1 nM, and 7.4±0.3 nM for Palvanil and capsaicin respectively) and acid (IC50 0.3±0.01 nM, and 3.8±0.06 nM for Palvanil and capsaicin respectively) pH. At the lower pH both compounds have a greater inhibitory activity, although Palvanil was 90-fold more potent at this pH, and capsaicin was only about 2-fold more potent. It is important to note that at both pH values, Palvanil has a remarkable inhibitory effect (>50%) at concentrations as low as 1 nM (FIG. 4A). Likewise, when using anandamide at a lower concentration (0.25 mM) the desensitizing effect of Palvanil was again more marked than that of capsaicin at acid pH (IC50 0.5±0.02 and 8.9±0.3 nM for Palvanil and capsaicin, respectively) (FIG. 4B).

Effect of Topical Capsaicin and Palvanil on Eye Wiping in the Mouse

Figure 5:
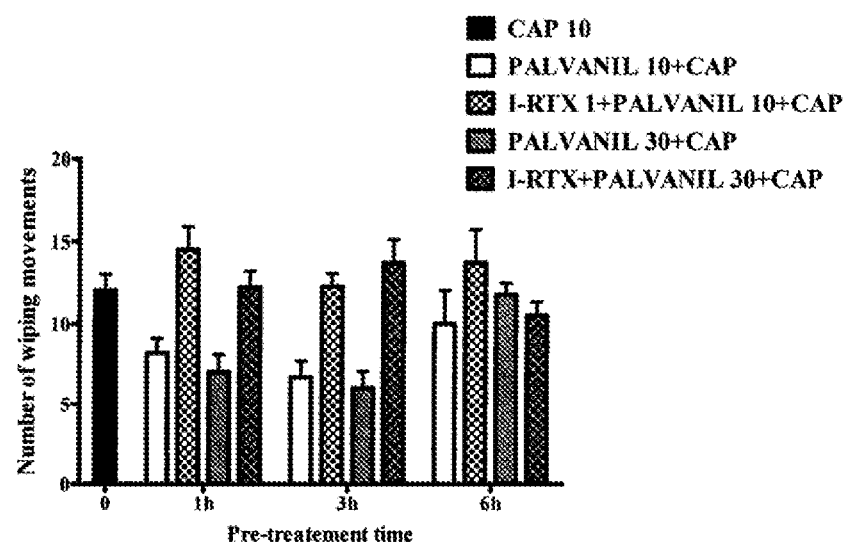
FIG. 5. Effect of Palvanil (10 e 30 μg/ml) alone or after 5'-iodo-resiniferatoxin (I-RTX) pre-treatment (1 μg/ml) on the number of wiping movements evoked by instillation of a capsaicin (CAP) solution (10 μg/ml) into the left eye. Palvanil was administered 1, 3 and 6 hours before capsaicin instillation, and I-RTX 30 minutes before Palvanil. Data are represented as means±S.E.M. of n=6 mice per group. * indicates P<0.05 vs. CAP-treated and ° P<0.05 vs. Palvanil-treated mice. One-Way ANOVA, post-hoc Tukey's.

The eye wiping test was employed as an in vivo pungency test in order to assess the pain-producing effects of topical Palvanil in the mouse. We found that instillations into the eye of Palvanil solution (10 and 30 g/ml) did not induce any eye-wiping reflexes in the mouse, indicating the complete lack of pungency for this compound (FIG. 5). On the contrary, the administration of capsaicin solution (10 μg/ml) evoked 12±0.9 wiping movements monitored within 30 seconds. However, Palvanil treatment (10 and 30 μg/ml), performed 1 and 3 hours before capsaicin in the same eye, significantly reduced the pain behavior to 8.2±0.9 and 6.7±0.7 and to 7.0±0.9 and 6.0±0.8, respectively (FIG. 5). This effect was completely reverted by pre-treatment with I-RTX (1 μg/ml) which did not cause any reflexes per se.

EXAMPLES OF PHARMACEUTICAL FORMULATIONS

Example 1

Cream for Application on Scarred Skin 100 g contain:

| | |
|---|---|
| Palvanil | g 0.50 |
| Vitamin E acetate | g 2.00 |
| Sodium hyaluronate | g 0.02 |
| Bronopol | g 0.005 |
| Hydrogenated Castor oil | g 1.50 |
| Noveon AA1 | g 1.60 |
| Water to | g 100.00 |

Example 2

Cream for Application on Healthy Skin 100 g contain:

| | |
|---|---|
| Palvanil | g 0.50 |
| PEG-5 plant sterols | g 4.50 |
| Stearic Acid | g 3.00 |
| Cetostearylic alcohol | g 3.00 |
| Adelmidrol | g 0.50 |
| Glyceryl monostearate | g 1.50 |
| Carbopol 940 | g 0.40 |
| 2,4-dichlorobenzylic alcohol | g 0.15 |
| Bronopol | g 0.05 |
| Water to | g 100.00 |

Example 3

Fluid Cream for Application on Broad Skin Areas 100 g contain:

| | |
|---|---|
| Palvanil | g 1.00 |
| Glycerine | g 5.00 |
| White mineral oil | g 3.00 |

-continued

| | |
|---|---|
| Silicone oil | g 1.00 |
| Glyceryl monostearate | g 1.40 |
| Cetostearylic alcohol | g 2.80 |
| Stearic acid | g 2.40 |
| PEG plant sterols | g 5.00 |
| Carbomer | g 0.10 |
| Bronopol | g 0.005 |
| Water to | g 100.00 |

Example 4

Gel for Oral Use 100 g contain:

| | |
|---|---|
| Palvanil | g 1.20 |
| Glycerine | g 10.00 |
| *Echinacea purpurea* glyc. Extract | g 10.00 |
| Sodium alginate | g 2.50 |
| Sodium Hyaluronate | g 0.02 |
| Triclosan | g 0.25 |
| Bronopol | g 0.005 |
| Water to | g 100.00 |

Example 5

Lotion for Trichological Use 100 g contain:

| | |
|---|---|
| Palvanil | g 0.50 |
| Adelmidrol | g 0.20 |
| D-biotine | g 0.04 |
| *Echinacea pupurea* glyc. Extract | g 10.00 |
| Ethyl alcohol | g 40.00 |
| Water to | g 100.00 |

Example 6

Vaginal Gel 100 g contain:

| | |
|---|---|
| Palvanil | g 0.50 |
| Glycerine | g 10.00 |
| Vitamin A palmitate | g 0.20 |
| 2-phenylethanol | g 0.15 |
| Hydrogenated Castor oil 40(OE) | g 1.00 |
| Methyl-paraoxybenzoate | g 0.05 |
| Noveon AA1 | g 1.00 |
| Sodium Hyaluronate | g 0.04 |
| Water to | g 100.00 |

Example 7

Gel for Balano-Preputial Use 100 g contain:

| | |
|---|---|
| Palvanil | g 0.25 |
| Glycerine | g 10.00 |
| Vitamin A palmitate | g 0.20 |
| 2-phenylethanol | g 0.18 |
| Bronopol | g 0.05 |
| Noveon AA1 | g 0.80 |
| Sodium Hyaluronate | g 0.04 |
| Water to | g 100.00 |

Example 8

Drops for Otological Use 100 g contain:

| | |
|---|---|
| Palvanil | g 0.30 |
| Transcutol P | g 49.00 |
| Propylene glycol | g 30.00 |
| Deo-Usnate | g 0.30 |
| Triclosan | g 0.20 |
| Phytosfingosin | g 0.15 |
| Trans-traumatic acid | g 0.06 |
| Water to | g 100.00 |

Example 9

Gel for Rectal Microclysma 100 g contain:

| | |
|---|---|
| Palvanil | g 0.25 |
| Glycerine | g 8.00 |
| Trans-traumatic acid | g 0.50 |
| 2-phenylethanol | g 0.10 |
| Hydrogenated Castor oil 40(OE) | g 1.00 |
| Methyl-paraoxybenzoate | g 0.05 |
| Noveon AA1 | g 0.50 |
| Water to | g 100.00 |

Example 10

Patch for Prolonged Dermal Application 100 cm$^2$ contain:

| | |
|---|---|
| Palvanil | mg 20.00 |
| Trans-traumatic acid | mg 2.00 |
| Adelmidrol | mg 10.00 |
| Gluing vehicle to | mg 80.00 |

Example 11

Gel for Periungual Use 100 g contain:

| | |
|---|---|
| Palvanil | g 0.50 |
| Trans-traumatic acid | g 0.10 |
| Sodium alginate | g 2.50 |
| Eumulgin L | g 1.00 |
| Undecylenic acid | g 0.25 |
| Bronopol | g 0.10 |
| Hyaluronic acid | g 0.10 |
| Water to | g 100.00 |

Example 12

Sterile Eyewash for Corneal Use 100 g contain:

| | |
|---|---|
| Palvanil | g 0.10 |
| Trans-traumatic acid | g 0.05 |
| Phosphate buffer 0.1M to | g 2.50 |

Example 13

Mouthwash for Oral Use 100 g contain:

| | |
|---|---|
| Palvanil | g 1.00 |
| Adelmidrol | g 0.50 |
| Trans-traumatic acid | g 0.05 |
| Glycerine | g 7.00 |
| Sodium Pyroglutamate | g 3.00 |
| Hydrogenated Castor oil 40(OE) | g 2.00 |
| Noveon AA1 | g 0.50 |
| Hyaluronic acid sodium salt | g 0.05 |
| 2,4-dichlorobenzylic alcohol | g 0.15 |
| Bronopol | g 0.10 |
| Water to | g 100.00 |

The invention claimed is:

1. A method for treating or ameliorating hyperalgesia caused by inflammatory or neuropathic conditions in a mammal comprising administering to the mammal a composition which comprises N-palmitoyl-vanillamide and trans-traumatic acid.

2. The method of claim 1, wherein the mammal is a human.

3. The method of claim 1, wherein the mammal is a cat or a dog.

4. The method of claim 1, wherein the inflammatory or neuropathic conditions are selected from the group consisting of: post-herpetic neuralgia, neuralgia of trigeminus, occipital neuralgia, dental neuralgia, glossopharyngeal, neuralgia, headache, uremic neuralgia, diabetic neuralgia, neuropathic itch, neurogenic itch, uremic itch, vulvodynia, vulvar vestibulitis, ano-rectal pain and itch, balanopreputial pain and itch, painful urogenital disorders, psoriasis-associated pruritus and pain, atopic dermatitis, itching skin diseases, muscular pain, pain of a tendon, osteoarthritis-associated pain, painful eye diseases, and inflammatory pathologies of the oral cavity.

5. The method of claim 4, wherein the inflammatory pathologies of the oral cavity are selected from the group consisting of: gingivitis, periodontitis, stomatitis, post implantation pain, and burning mouth syndrome.

6. The method of claim 4, wherein the inflammatory pathologies of the oral cavity are selected from the group consisting of: canine and feline gingivitis, periodontitis, gingivostomatitis, and feline resorptive lesions (FORL).

7. The method of claim 1, wherein the composition is in the form of a topical composition.

8. The method of claim 7, wherein the topical composition is a cream, gel, lotion, drops for otological application, patch, eyewash, mouthwash or suppository.

9. The method of claim 7, wherein the composition comprises from about 0.05% to about 5% w/w of N-palmitoyl-vanillamide.

* * * * *